United States Patent [19]
Fritzsch et al.

[11] Patent Number: 5,766,169
[45] Date of Patent: Jun. 16, 1998

[54] MEDICAL MULTIFUNCTIONAL INSTRUMENT FOR PERFORMING ENDOSCOPIC OPERATIONS

[75] Inventors: Gernod Fritzsch, Tuttlingen; Michael Lurz, Dürbheim, both of Germany

[73] Assignee: Delma elektro-und medizinische Apparatebau Gesellschaft mbH, Tuttlingen, Germany

[21] Appl. No.: 490,501

[22] Filed: Jun. 13, 1995

[30] Foreign Application Priority Data

Jun. 13, 1994 [DE] Germany .......... 44 20 608.9

[51] Int. Cl.$^6$ .................................. A61B 17/36
[52] U.S. Cl. .................................. 606/48; 606/46
[58] Field of Search .......... 600/125, 136–137; 606/41–50, 51–52; 607/95

[56] References Cited

U.S. PATENT DOCUMENTS

| | | |
|---|---|---|
| 4,762,120 | 8/1988 | Hussein .................. 600/136 |
| 4,911,148 | 3/1990 | Sosnowski et al. .......... 600/136 |
| 5,254,177 | 10/1993 | Rigby et al. ............... 606/46 |
| 5,366,476 | 11/1994 | Noda ................. 606/48 X |
| 5,449,357 | 9/1995 | Zinnanti .............. 606/45 X |

*Primary Examiner*—Jennifer Bahr
*Assistant Examiner*—Ryan Carter
*Attorney, Agent, or Firm*—Townsend and Townsend and Crew LLP

[57] ABSTRACT

A multifunctional instrument for performing endoscopic operations has an operator hand grip (11) and an instrument socket (12) on which an instrument body (13) with a multilumen tube (14) which can be guided through a trocar is mounted. The operator hand grip (11) extends transverse to the central axis (15) of the instrument body (13). The instrument body (13) is rotatable about the central longitudinal axis (15) relative to the instrument socket (12), which is fixedly connected to the operator hand grip (11), and securely holdable in the selected rotational position.

35 Claims, 5 Drawing Sheets

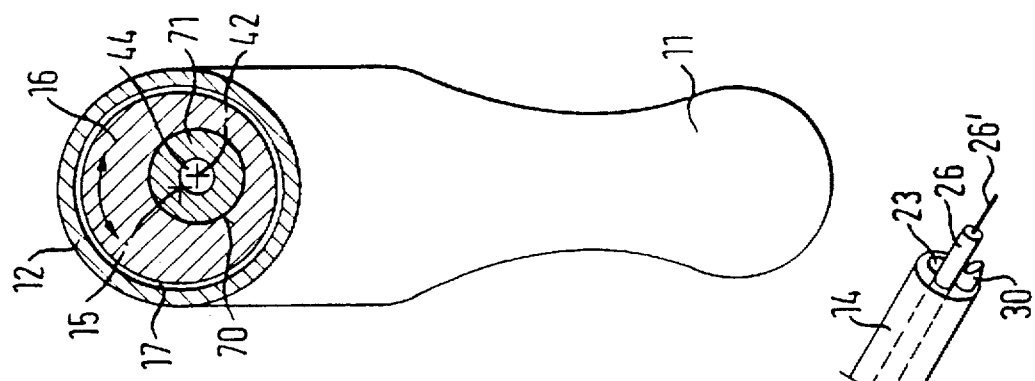
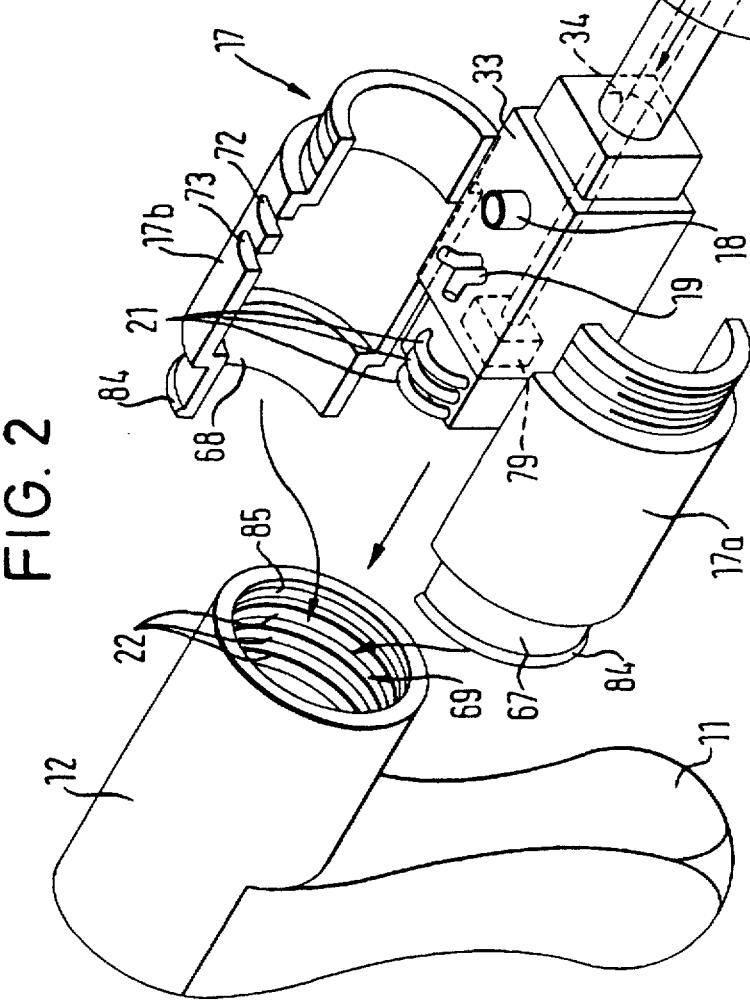

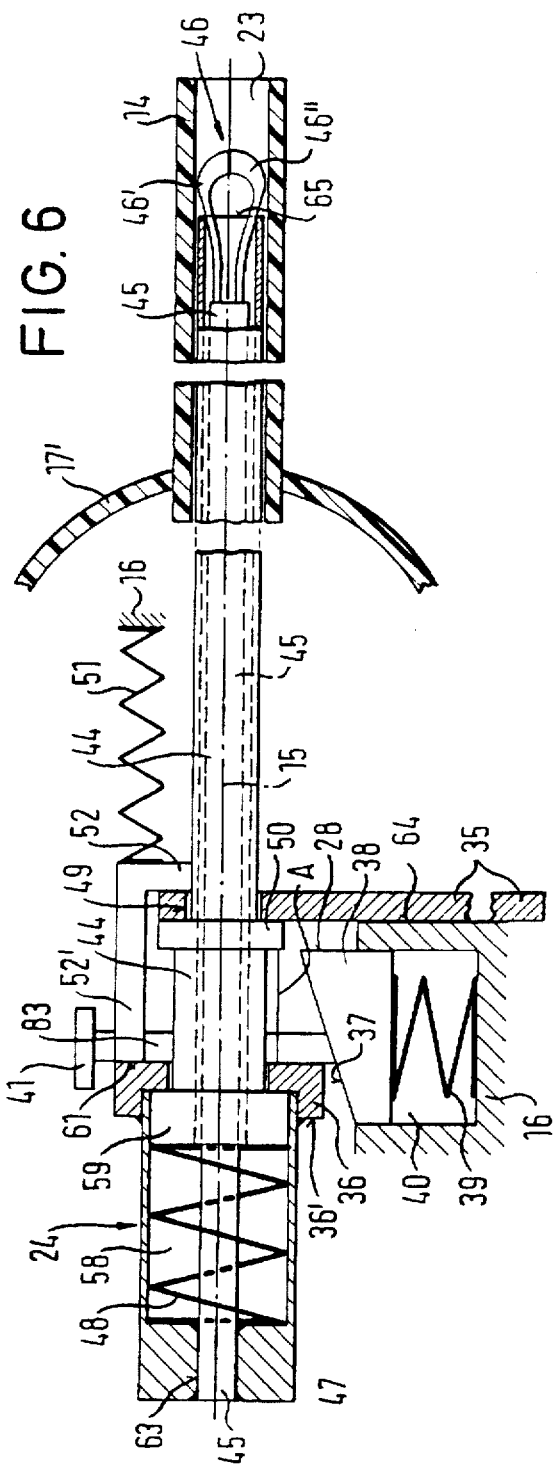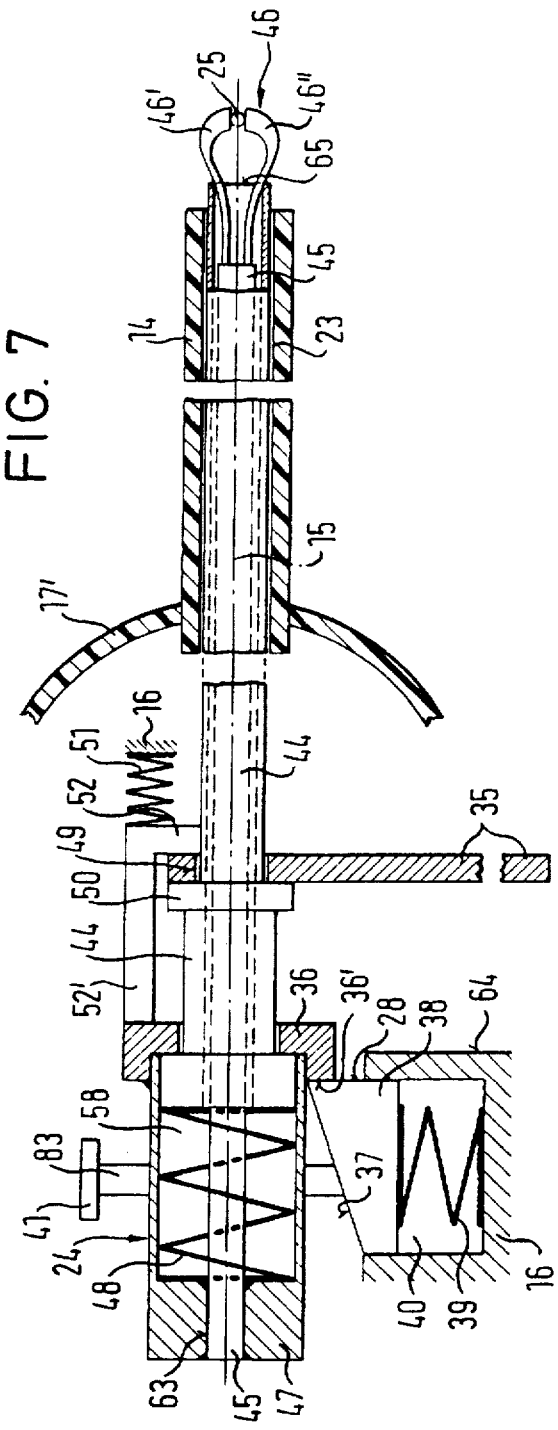

MEDICAL MULTIFUNCTIONAL INSTRUMENT FOR PERFORMING ENDOSCOPIC OPERATIONS

BACKGROUND OF THE INVENTION

1. Field of the Invention

The invention relates to a medical multifunctional instrument for performing endoscopic operations in accordance with the preamble of patent claim 1.

2. Description of the Prior Art

Multifunctional instruments of this kind of many different designs are known (see e.g. EP 0 327 410 A1). A problem with these multifunctional instruments is that the operator must, on the one hand, be able to securely hold the instrument but, on the other hand, be able to bring the various working tools as well as the suction and flushing channels arranged around the instrument axis into an optimum position for performing the treatment. The handling is made even more difficult due to the fact that, in general, there are different actuation elements arranged on the operator hand grip which the operator needs to be able to actuate without jerking the instrument.

SUMMARY OF THE INVENTION

A first object of the invention is to provide a multifunctional instrument of the initially named kind, the working tools of which and optionally the suction and flushing channels of which can be brought into the desired rotational position around the axis of the tube without the operator's secure hold being compromised.

A first inventive concept is that the operator hand grip is formed in a manner of a pistol grip extending transverse to the tube so that the instrument can be securely held by the operator in a relaxed and ergonomically advantageous manner. The operator hand grip thus forms a compact unitary body similar to the hand grip on a pistol butt. Several mobile actuation elements are arranged on the grip such that their use does not compromise the operator's secure hold of the operator hand grip. As a result of the form of the instrument in accordance with the invention, the operator hand grip can only be optimally held in a very particular direction by the surgeon standing next to the patient. Because of this, the invention provides a relative rotatability between the instrument body and the instrument socket. This allows the different channels at the distal end of the tube to be brought into the optimum rotational position relative to the tube axis for the operation to be performed, thus ensuring that the operator hand grip does not have to be rotated out of the optimum gripping position. The surgeon can thus grip the multifunctional instrument of the invention in a secure and ergonomically problem-free manner and can simultaneously bring the various channels into the optimum treatment position. The rotatability is of importance when the working tool or the flushing or suction aperture are arranged non-rotationally symmetrically and/or eccentrically.

An eccentric arrangement is limited, in particular when a plurality of working channels as well as at least one suction or flushing channel are to be accommodated, by the fact that for surgical reasons the outer diameter of the tube 14 is limited to approximately 10 mm so that the various channels need to be arranged in a relatively small cross-section in such a manner that they can have as large a diameter as possible. To do this, an eccentric arrangement of practically all the channels is necessary.

A rotational position which has been selected by rotating the instrument body relative to the operator hand grip can most easily be secured by a certain amount of friction between these two components, this friction being small enough to allow rotation on the application of a moderate amount of force which is however large enough to avoid slippage during normal use of the instrument.

It is advantageous that the connection lines are rotated in the direction towards the separately provided supply device so that the spatial limitations imposed by the operation can also be adjusted to in an optimum manner. This embodiment is above all advantageous when the working channel is arranged concentrically in the tube so that the rotational degree of freedom can be exploited for an optimum positioning of the connection lines.

However, even when a rotational degree of freedom is not available for the correct rotational position of the connection lines and the supply and removal lines, such an embodiment is advantageous because then the intermediate pieces of the line which move on rotation between instrument body and operator hand grip can be dispensed with, whereas such intermediate pieces would otherwise be necessary if the connections were positioned on the instrument socket.

A further embodiment is useful when actuation elements for electrical and/or hydraulic and/or pneumatic switching are provided on the operator hand grip. The wiper to slip ring contacts can be dispensed with when the electrical control lines for the keypad arranged on the operator hand grip are directly fed into the operator hand grip or the instrument socket. However, since it is preferred to feed the fluid supply and removal lines laterally into the connection body, it is useful to feed the electrical control lines in and out there as well so that feed-in and feed-out lines are only present at one position of the instrument.

A further object of the invention is to provide a multifunctional instrument of the initially named kind in which a separate working instrument can be inserted externally and then moved into a working position and a rest position as easily and as effectively as possible.

The working instrument can on the one hand be connected to the instrument socket or the instrument body so as to be absolutely fixed axially, whereas on the other hand an automatic return into a retracted rest position is effected by actuating the release device and the subsequent action of resetting spring force.

An actuation lever is of particular advantage because it can be actuated in a particularly ergonomically advantageous manner in conjunction with the pistol-grip form of the operator hand grip.

A further embodiment has a particularly preferred construction for the form of the latch spring arrangement for holding the working instrument in the working position and for its automatic release into the rest position.

A further object of the invention is to remedy the disadvantages associated with the eccentric arrangement of the working channel or working channels when performing endoscopic observations, these disadvantages being in particular that the working tool or tools can often not be optimally viewed when holding the instrument socket in a particular position, wherein the solution should not compromise the problem-free insertion and removal of a working instrument.

As a result of this design, the connection body or the tube can be rotated about the rotational axis relative to the instrument socket and in particular to the operator hand grip, which is preferably arranged in the manner of a pistol, into a position such that the working tool, which can protrude from the front of the tube, can be viewed in an optimum manner through an endoscope, wherein the cam effects an axial alignment of the working channel and its extensions in every position.

When the working instrument is retracted, i.e. withdrawn, the main working channel can be used as a flushing or suction channel. This makes it possible to remove larger biological tissue fragments, concrements and hard tissue particles.

A further object of the invention is to design the multifunctional instrument of the invention to be even more universal without thereby making the handling more difficult.

Thus, in accordance with the invention, as well as the provision of a preferably large-lumen main working channel with a working instrument which is retractable into this channel, a further preferably small-lumen working channel is provided in which a further rod-like instrument is arranged which can be retracted into a rest position and extended out into a working position. With this design, the one or the other working tool can be extended out of the tube as desired. Both working channels should be straight.

Whereas the main working instrument is preferably inserted from the rear by hand and snapped into the working position and prior to this or subsequent to this optionally rotated into the desired position, the second working instrument is normally arranged fixed in the connection body and in the tube. The second working instrument is, however, removable and is extended out into the working position or retracted into the tube to the rest position by means of a drive provided in the connection body. This drive can, for example, be pneumatic, hydraulic or electromagnetic and is actuatable in a defined manner via an actuation element of the keypad.

Finally, a further object of the invention is to be able to flush free and to suck free the tissue positions which come into contact with the working tools in an aligned and directed manner.

In a further embodiment the flushing jet is directly pointed onto the operation site or secretions are directly sucked away from the operation site.

A particularly versatile multifunctional instrument can be provided by combining one or more of the described solutions.

BRIEF DESCRIPTION OF THE DRAWING

FIG. 2 is a perspective exploded view of a preferred construction of a multifunctional instrument of the invention, wherein inside the tube and the connection body only the small-lumen second working channel and the rod-shaped radio frequency cutting or coagulation instrument arranged therein and its drive are shown (in broken lines);

FIG. 3 is a schematic sectional view through the line III—III in FIG. 1;

FIG. 6 is a purely schematic side view of the fixing and displacement mechanism for a working instrument inserted from the rear inside the cam of the multi-functional instrument in accordance with FIGS. 1 to 5, shown after insertion in the rest position directly after the coming into engagement of the working instrument with the complementary components of the cam and of the instrument socket;

FIG. 7 is a view of the fixing and displacement mechanism corresponding to FIG. 6 in the more deeply inserted snapped-in working position of the working instrument, wherein the active position of the working tool is regained when the guide tube is slid forward.

DETAILED DESCRIPTION OF THE PREFERRED EXEMPLARY EMBODIMENTS

Figure 1:
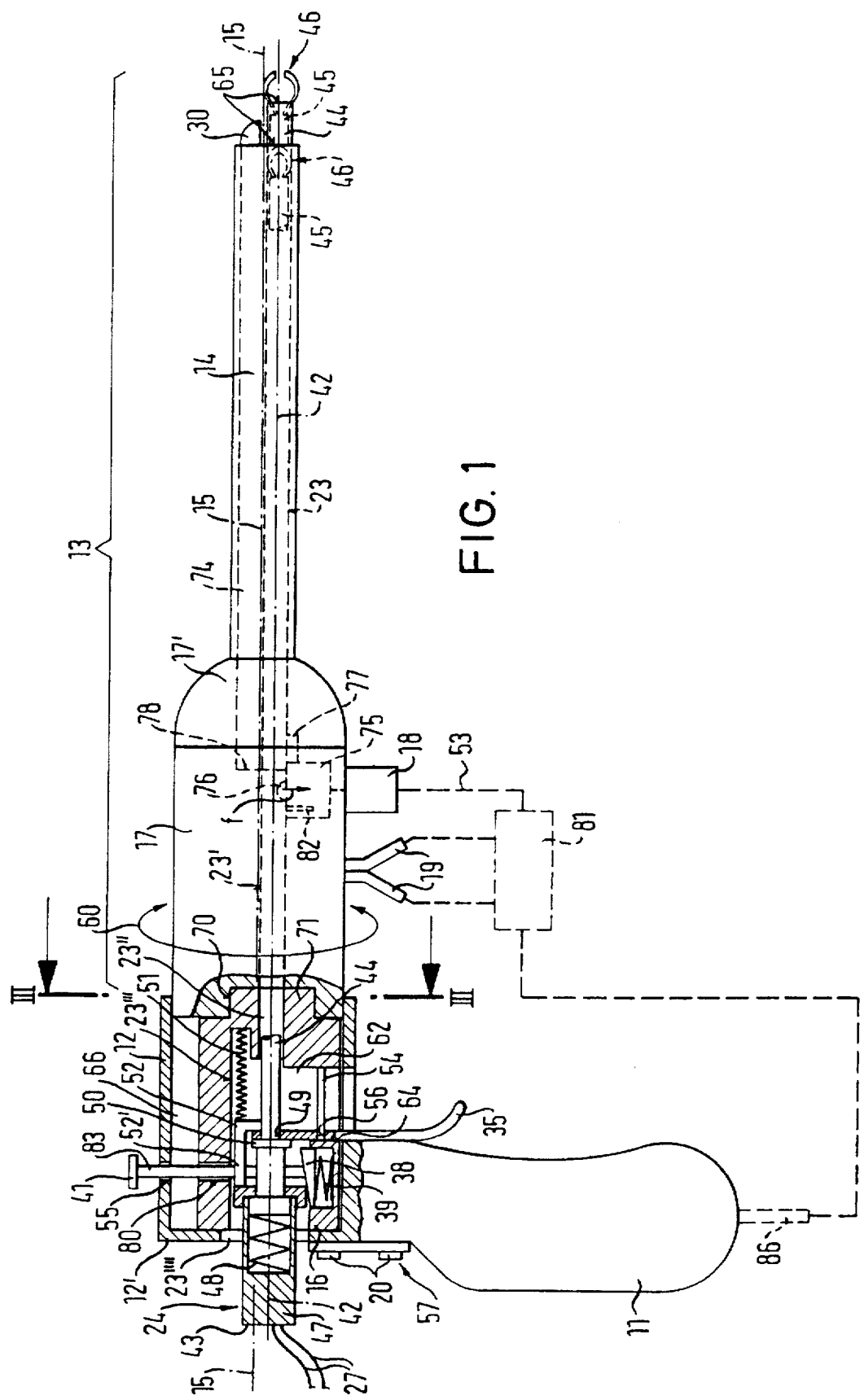
FIG. 1 is a schematic side view of a multifunctional instrument of the invention, wherein in the connection body in the tube only the working channel containing a working instrument and, in broken lines, the liquid flushing or suction channel are shown.
Figure 5:
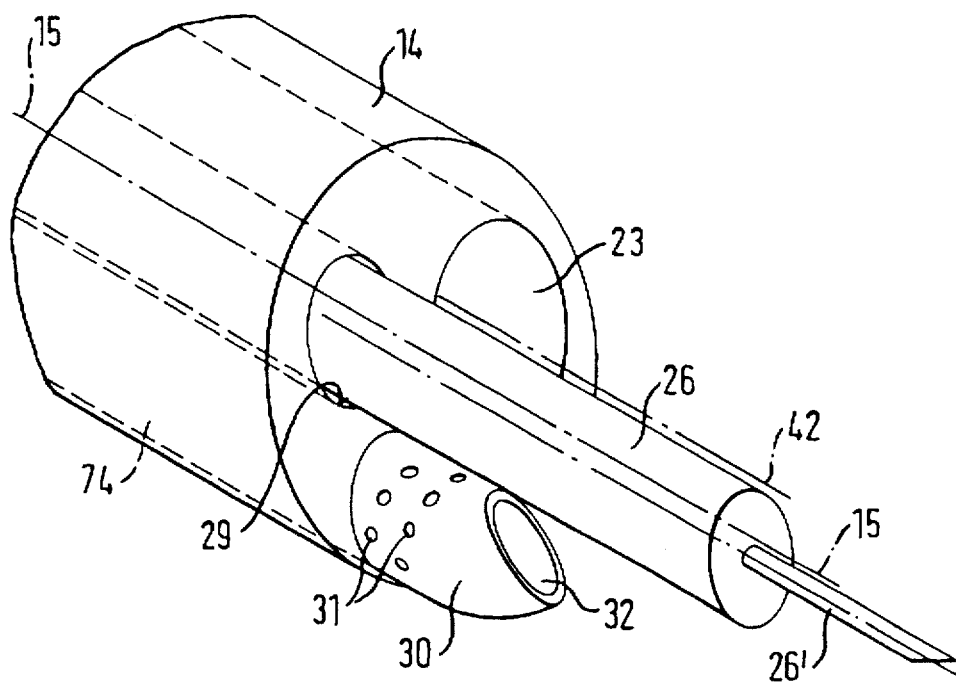
FIG. 5 is a heavily enlarged schematic perspective view of the distal end of the tube of a preferred embodiment of the multifunctional instrument of the invention without the main working instrument in place.

As shown in FIG. 1, a multifunctional instrument in accordance with the invention comprises an instrument body 13 which has a substantially cylindrical connection body 17 with a screw cap 17' arranged on the front of it and a multilumen plastic tube 14 with a central axis 15 which projects axially out of the front of the screw cap 17', the plastic tube 14 comprises, as shown in FIGS. 1, 2 and 5, an eccentric large-lumen first working channel 23 with a central axis 42 extending parallel to and laterally spaced apart from the axis 15, as well as, parallel thereto, an eccentric small-lumen second working channel 29 and a liquid flushing and/or suction channel 74. FIG. 1 only shows the first working channel 23 and the flushing and/or suction channel 74 (in broken lines). The second working channel 29 is not shown in FIG. 1 for the sake of clarity. In FIG. 2, for the sake of clarity, only the second working channel 29 in the tube 14 is drawn in (in broken lines), while only the spout and an extension 30 protruding from the front of the tube 14 are shown of the two other channels 23, 74. The working channel extends in the connection body 17 into a channel extension 23'.

As shown in FIG. 1, a guide tube 44 of a working instrument 24 is inserted into the working channel 23 of the tube 14 passing through from the rear to the front. The front end carrying a working tool 46 is shown in broken lines in a retracted rest position and in solid lines in a working position extended out of the front of the tube 14. As shown in FIGS. 2 and 5, a rod-like radio frequency cutting and/or coagulation instrument 26 is incorporated into the second working channel 29, the distal end of which, which is provided with a cutting needle 26', projects forwardly out of the front surface of the tube 14 and thus adopts a working position from which it can, however, be withdrawn rearwardly into the second working channel 29 in the manner described in more detail below, so that the front part of the instrument 26 including the cutting needle 26' disappears completely in the second working channel 29.

Figure 4:
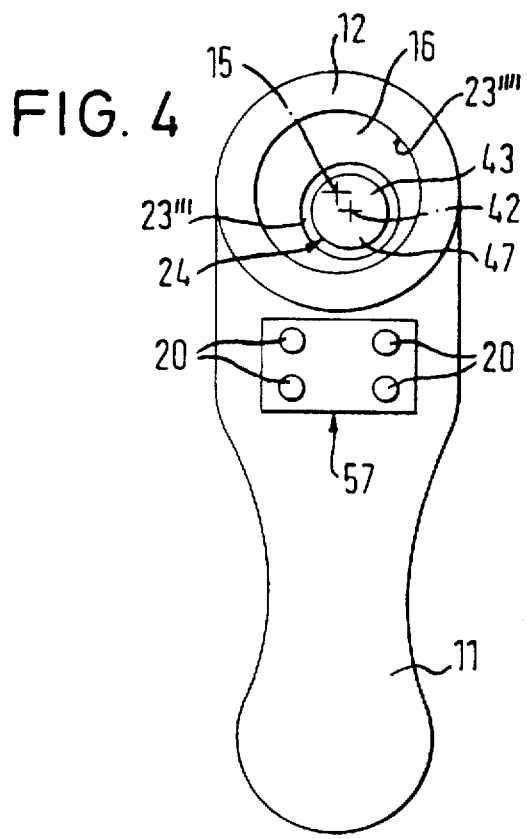
FIG. 4 is a rear view of the multifunctional instrument of FIG. 1.

The connection body 17 is secured rotatably on the instrument socket 12 which is also constructed substantially cylindrically. An operator hand grip 11 extends away from the instrument socket 12 rearwardly substantially at a right angle to the central axis 15. Actuation elements 20 for electrical and/or hydraulic and/or pneumatic control are collected together on a keypad 57 and located on the rear side of the operator hand grip 11 (FIGS. 1, 4). As shown in FIGS. 1 and 2, a fluid supply and removal line arrangement 18 and electrical control and/or supply cables 19 which lead to a control device 81 (only indicated in broken lines in FIG.

1) open out radially in the connection body 17. The fluid supply and removal line arrangement 18 is also connected in the manner indicated in broken lines in FIG. 1 via a connection line 53 to the central control device 81.

The fluid supply and removal line arrangement 18 is connected to a changeover valve 75 (indicated in FIG. 1 with the dashed line) in the inside of the connection body 17 and permits a selective connection between the fluid supply line arrangement and the fluid removal line arrangement 18 on the one hand and, on the other hand, via a connection line 78 to the flushing and/or suction channel 74 provided in the connection body 17 and the tube 14 or via a connection line 77 with the inside of the first working channel 23 or its extension 23'. When no working instrument 24 is accommodated in the first working channel 23 or its extension 23', an actuation projection 76 of the changeover valve 75 protrudes in the manner indicated with the dashed line in FIG. 1 into the extension 23' of the working channel 23 which is slid back in the direction of the arrow f by the inserted working instrument 24, whereby the liquid supply or removal which was initially present between the line arrangement 18 and the connection lines 78 is interrupted and between the line arrangement 18 and the connection line 77 is opened. In other words, in all cases when no working instrument 74 is situated in the working channel 23, the latter is used as a suction and/or flushing channel. In order that, in the last mentioned case, the working channel 23 is closed at the back, a closure member 82, which can be part of the valve mechanism, passes, after withdrawal of the working instrument 24 out of the working channel 23 or its extension 23' in the connection body 17, automatically into the channel extension 23' so that liquid entering via the connection line 77 is forced to flow to the distal end of the working channel 23.

The suction and/or flushing channel 74 opens out at the distal end of the plastic tube 14 into the short tubular extension 30 which has lateral relief bores 31 and whose spout 32 is arranged forming an angle relative to the central axis 15 such that a flushing jet being emitted there is directed towards those regions which are to be treated by a working tool 26', 46 which is situated in its working position as shown in FIG. 5.

As shown in FIGS. 1, 3 and 4, a substantially cylindrical hollow cam or eccentric member 16 is arranged in the instrument socket 12 concentrically to the central axis 42 of the first working channel 23, i.e. eccentric to the rotational axis 15, and comprises at its front a concentric guide spigot 71 which rotatably engages a rear eccentric receiving bore 70 of the connection body 17 and slidingly contacts the back wall 12' of the instrument socket 12 with its rear end face. As a result among other things of the radial actuation pin 83 of a release button 41 described further below which passes through a radial bore 55 into the instrument socket 12 and through a radial bore 80, the cam 16 is held against a substantial rotation within the instrument socket 12. It can, however, be radially displaced within a clearance space 66 provided in the cavity of the instrument socket 12 such that the central axis of the cam, which is identical to the central longitudinal axis 42 of the working channel 23, can perform an orbital movement around the rotational axis 15 without the cam 16 itself turning substantially.

The working channel 23 of the tube 14 and its extension 23' pass at the back axially into a correspondingly dimensioned extension 23" inside the guide spigot 71 with a cavity 23"', representing a further extension of the working channel 23, adjoining the extension 23" inside the cam 16. At the rear, the extension 23"' ends in a large aperture 23"" in the rear wall 12' of the instrument socket 12.

When the connection body 17 carrying the tube 14 rotates about the central axis 15 of the tube 14 and of the connection body 17, the central axis 42 of the receiving bore 70 rotates about the rotational axis 15 and thus takes the cam 16 with it in a corresponding eccentric orbital movement. The working channel 23 in its extension 23' in the connection body 17 thus remain aligned at all times with the further extensions 23" and 23"' in the cam 16 so that in any position of the connection body 17 a rod-like working instrument 24 can be inserted from the rear to the aperture 23"' in the position evident from FIG. 1 inside the working channel arrangement 23, 23', 23", 23"', 23"".

The proximal end 43 of the working instrument 24 protrudes through the central aperture 23"" from the rear end of the instrument 12 and serves for mounting any electrical and/or hydraulic and/or pneumatic supply and removal lines 27 that are required. In the present embodiment, a radio frequency voltage for coagulation can be applied to the connection lines 27 which can then be conducted to two coagulation clamping electrodes 46', 46" at the front working end forming the working tool 46 via lines laid in a central working rod 45 of the working instrument 24 in the manner described further below with reference to FIGS. 6 and 8.

As shown in FIG. 2, the connection body 17 is made up of two shell halves 17a, 17b which are held together on one end by insertion into the tubular instrument socket 12 and on the other end by the screw cap 17 mounted thereon. A rotational connection is present between the instrument socket 12 and the shell halves 17a, 17b axially installed there, for which purpose semi-cylindrical spigot parts 67, 68 engage from the rear end of the shell halves 17a, 17b into a central concentric bore 69 at the front end of the instrument socket 12. The axial fixing of the housing shell halves 17a, 17b placed in the instrument socket 12 is achieved by beads 84 provided at the periphery of the spigot parts 67, 68 which engage in recesses 85 complementary thereto at the inner periphery of the hollow cylindrical instrument socket 12 in the region of the receiving aperture 69. The shell halves 17a, 17b enclose between them a connection part 33 in a fixed manner. This connection part 33 has an axial bore 34 for the receipt of the tube 14 which is preferably designed to be removable and moreover carries resilient wiper contacts 21 which, after the assembly of the instrument, come into electrically conducting contact with slip rings 22 provided at the inner wall of the tubular instrument socket 12. In this manner, even when the connection body 17 formed from the shell halves 17a, 17b rotates, the electrical control and switching functions are transmitted from the actuation element 20 on the operator hand grip 11 to the connection part 33.

Passage slots 72, 73 are situated in the housing shell half 17b, are open towards an edge and are constructed to be complementary to the fluid supply and removal lines 18 and to the electrical supply and control lines 19 projecting from the connection part 33 so that, after assembly, the lines 18, 19 project radially out of the passage slots 72, 73.

To the extent that the actuation elements 20 (FIGS. 1, 4) are intended also to include hydraulic and/or pneumatic switches or control elements, hydraulic lines may also extend from the instrument socket 12 into the rotatable connection body 17. The hydraulic lines are laid out or made flexible such that they can still perform their function even when there is a relative rotation between the instrument socket 12 and the closure body 17. In principle, it is also conceivable that the control lines at 86 in FIG. 1 connected to the actuation elements 20 of the keypad 57 could also be led out of the operator hand grip 11 and from there to the control device 81.

As shown in FIGS. 1 and 6 to 8, a particularly preferred embodiment of a working instrument 24 comprises a right cylindrical base part 47 which is situated right at the back of the instrument and which at its front end comprises a cylindrical cavity 58 in which a piston 59 is arranged which is urged forwardly by a spring 48 and from which the guide tube 44 extends forwardly, the guide tube 44 passing right through the working channel 23 and its extensions 23', 23", 23"' and being held there in a rotatable and axially displaceable manner. A working rod 45, which is axially movable relative to the guide tube 44 and which is fixedly connected to the base part 47, extends through the guide tube 44, the piston 59, the spring 48 and optionally a corresponding axial bore 63 in the base part 47 up to the front edge 65 of the guide tube 44 where the working tool 46 comprised of the two clampable electrodes 46', 46" of a radio frequency coagulation instrument projects forwardly from the working rod 45.

A latch collar 36 is provided at the front end of the base part 47, while the guide tube 44 carries an abutment collar 50 at a distance A (FIG. 6) in front of the latch collar 36 (when the piston 59 is situated in the foremost position).

Figure 8:
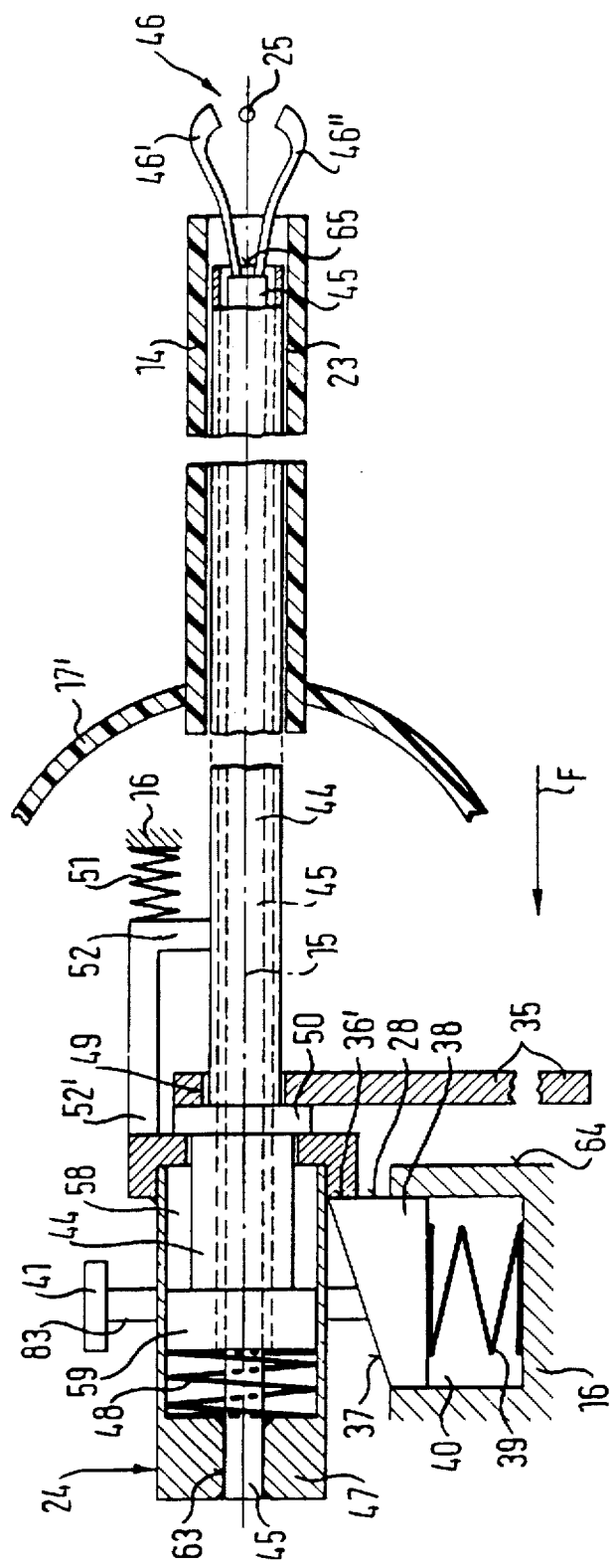
FIG. 8 is a view analogous to FIG. 7 for a working instrument which has been moved into its inactive position by pulling the actuation lever.

The abutment collar 50 cooperates with a transversely displaceable latching element 38 arranged in the cam 16 which is radially inwardly biased by a deployment spring 39 onto the latch collar 36 and carries an inclined plane 37 at its radially inner side up which the latch collar 36 travels when the working instrument 24 is inserted from the rear into the working channel arrangement 23, 23', 23", 23"', 23"" in accordance with FIGS. 6 and 7. In so doing, the latch collar radially outwardly displaces the latching element 38 within a radial guide 40 provided in the cam 16 against the force of the spring 39 as shown in FIGS. 6 to 8.

As soon as the latch collar 36 has reached the front end of the latching element 38, the latter snaps under the action of the spring 39 in accordance with FIG. 7 behind the rear end face 36' of the latch collar 36 extending perpendicular to the central axis 15 so that the front end face 28 of the latching element 38 which also extends perpendicular to the central axis 15 comes into engagement with the end face 36' which makes a movement of the working instrument 24 backwards impossible until the latching element 38 is brought once more out of engagement with the latch collar 36 by radially pressing a release button 41 (FIGS. 1, 6 to 8) which is accessible from the outside and which is connected to the latching element 38 via the radial actuation member 83. The actuation member 83 extends through the radial bore 55 in the peripheral wall of the instrument socket 12 with a sufficient amount of angular clearance to allow it to follow the tilting movement which occurs as a result of the orbital eccentric movement of the cam 16.

The limitation of the movement of the working instrument 24 in the forward direction is provided by the abutment of the front surface 61 of the latch collar 36 against an axial projection 52' of an abutment collar engagement holder 52 which is braced at the front against the cam 16 by a spring 51 and which is a component of the cam 16.

In this manner, the latch collar 36 on travelling up the inclined plane 37 with radially outward displacement of the latching element 38, simultaneously pushes the abutment collar engagement holder 52 forwardly while compressing the spring 51 into the forward end position shown in FIG. 7. In this manner, the working instrument 24 is fixed forwardly in the working position shown in FIG. 7 by the correspondingly compressed spring 51 and backwardly by the latching element 38.

As shown in FIGS. 1, 6 and 7, an actuation lever 35 is arranged in front of the abutment collar 50 on the guide tube 44 by means of a correspondingly dimensioned bore 49 and, as shown in FIG. 1, protrudes downwards out of a corresponding recess 62 of the cam 16 and of the instrument socket 12 parallel to the operator hand grip 11, and indeed in a manner such that, when the operator hand grip 11 is being held, it can be gripped by the index finger of the operator like the trigger of a pistol.

In accordance with FIG. 6, the actuation lever 35 is loaded at its end region situated in the cam 16 from the rear by the abutment collar 50, whereas the abutment collar engagement holder 52, which is urged rearwardly by the spring 51, engages on the actuation lever from the front, whereby the actuation lever 35 is resiliently held in the position shown in FIG. 6 between the components 50 and 51. The spring 51 biases the actuation lever 35 via the abutment collar engagement holder 52 against an abutment surface 64 of the cam 16 so that the actuation lever 35 contacts the abutment surface 64 when the working instrument 24 is retracted in the rest position in accordance with FIGS. 1 and 6.

The actuation lever 35 is moreover guided in an axially displaceable manner on the instrument socket 12 which is only indicated schematically in FIG. 1. For this purpose, a guide rod 54 fixed in the socket is shown in FIG. 1 in the recess 62 and engages through a complementary guide bore 56 in the actuation lever 35.

As shown in FIG. 2, the second, smaller working channel 29 extends within the tube 14 and the connection part 33 of the connection body 17 up to a drive 79 which is only indicated schematically in broken lines. This drive can, for example, be a pneumatic reciprocating piston arrangement with which the rod-like working instrument 26 with the radio frequency cutting needle 26', which is inserted from the front into the working channel 29, can be brought into engagement such that, on corresponding actuation of the drive 79 by actuating the pressure button 20 of the keypad 57 (FIGS. 1, 4) provided for this, the working instrument 26 can be selectively extended out of or withdrawn back into the front end of the tube 14.

The function of the working instrument 24 is described in the following with the aid of FIG. 1 and FIGS. 6 to 8:

When the working instrument 24 is not in place, the spring 51 presses the actuation lever 35 via the abutment collar engagement holder 52 into the most rearward position visible in FIGS. 1 and 6 where the actuation lever 35 contacts for example an abutment surface 64 of the cam 16 from the front.

If now the working instrument 24 is inserted from the rear into the working channel arrangement 23, 23', 23", 23"', 23"", the guide tube 44 passes through the bore 49 of the actuation lever 35 through into the position visible in FIGS. 1 and 6 where the latch collar 36 has come into engagement with the projection 52' and also the abutment collar 50 has come into engagement with the actuation lever 35 from behind. This is the rest position of the working instrument 24 illustrated in FIG. 1 in which the working tool is retracted into the front end of the tube in accordance with FIG. 6 and the dashed line in FIG. 1.

If the working instrument 24 is now displaced further forward in the instrument socket 12 or the cam 16, the abutment collar 50 takes the abutment collar engagement holder 52 with it via the actuation lever 35 while the resetting spring 51 is compressed. The latch collar 36 slides up the inclined plane 37 of the latching element 38 and thus pushes back the latching element 38 inside its radial guide 40 until finally it snaps into the working position visible in FIG. 7. During the pushing of the working instrument 24 out of the rest position of FIG. 6 into the working position of FIG. 7, the working tool 46 which is initially retracted in the front end of the tube 14 moves out of the position illustrated in FIG. 6 and shown in broken lines in FIG. 1 into the working position and protrudes out of the front end of the tube 14 as is evident from FIG. 7 and as is illustrated by the solid lines in FIG. 1. In this position, the actuation lever 35 is, as before, clamped between the abutment collar 50 and the abutment collar engagement holder 52, namely as a result of the reaction of the resetting spring 51 which is now compressed to its maximum degree.

That is to say, during the displacement from the rest position of FIG. 6 into the working position of FIG. 7 the actuation lever 35 also travels forwards so that now, as shown in FIG. 8, it can be displaced rearwardly on retraction of the finger in the direction of the arrow F, taking with it the guide tube 44. The guide tube 44 with the piston 59 thus travels back as well while the spring 58 is pressed together. In this position, the resilient clamping electrodes 46', 46" adopt the unclamped position shown in FIG. 8 so that the electrodes 46', 46" can be guided, for example, over a tissue part 25 which is only schematically indicated.

If now the amount of finger force exerted in the direction of the arrow F onto the actuation lever 35 is reduced by a given amount, the spring 48 compressed on the pulling back of the actuation lever 35 pushes the piston 59 and thus the guide tube 44 forwards once again, wherein the front edge 65 of the guide tube 44 slides along the electrodes 46', 46" which are slightly resiliently outwardly splayed and thus tension the electrodes together in the manner of pliers as shown in FIG. 7. The tissue part 25 is thus clamped and can now be coagulated in the desired manner by switching on the high frequency coagulation current. The clamping can be released on retraction of the actuation lever 35 once again into the position of FIG. 8.

If the working instrument 24 is to be transferred from the non-actuated working position of FIG. 7 into the retracted rest position of FIG. 6, the release button 41 is pressed whereupon the latching element 38 comes out of engagement with the latch collar 36 and the spring 51 pushes back the working instrument 24 via the abutment collar engagement holder 52 and its projection 52'. The working tool 46 of the working instrument 24, which hitherto projected out of the front end of the tube 14 in accordance with FIG. 7 as also shown by the solid lines in FIG. 1, is then drawn back inside the working channel 23 in accordance with FIG. 6 into the retracted position, indicated with the dashed line in FIG. 1. The working instrument 24 can remain in this rest position until it is required for further treatment. It can however also be completely withdrawn from the instrument socket 12 in the instrument body 13 rearwardly from this relaxed retracted position. The actuation element 76 (FIG. 1) is released and thus the working channel 23, which is now free, can automatically be used as a suction or flushing channel on closure by means of the displacer 82 and connection via the line 77 to the fluid supply and removal line 18.

The working instrument 24 fitted into the instrument socket 12 in the instrument 13 in accordance with FIG. 1 can, as also the closure body 17 itself, be rotated into a desired position in the sense of the double arrow 60 in FIG. 1 in both directions.

As a result of the design of the invention, the following types of work can be performed with the multifunctional instrument of the invention:

The large working channel 23 is used as the suction or flushing channel when the working instrument 24 is not in place, whereas the working instrument 26 with the cutting needle 26' can be extended out into the working position as shown in FIG. 5 by actuating the drive 79 by means of the associated keys 20 of the keypad 57 (FIG. 2). The normal suction or flushing channel 74 is in this case not available for use.

The working instrument 24 can however already be inserted into the instrument and into the rest position shown in FIG. 1 in which the working tool 46 is situated in the retracted position inside the working channel 23 illustrated by the dashed lines during the above-described working process. In this case, the fluid supply and removal line 18 is switched off from the working channel 23 by the valve 75 and connected to the smaller suction and flushing channel 74 which, in this manner, can perform its function via the tube extension 30 in accordance with FIG. 5.

If the working instrument 46 is now to be used, the working instrument 26 is initially retracted into the working channel 29 by actuating the drive 79 (FIG. 2) by means of the corresponding key 20, and the working tool 46 is then extended out of the tube 14 forwards into the position shown in FIG. 7 by inserting and snapping in the working instrument 24. The working instrument 46 can then be brought into the desired position relative to the rotational axis 15 by rotating the connection body 17. The working instrument 24 can moreover also be brought into the desired rotational position about its axis 42.

By pulling on the actuation lever 35 to bring it into the position shown in FIG. 8, the guide tube 44 is withdrawn, whereby the front edge 65 of the guide tube 44 slides back on the outer edge of the two branches 46', 46" and these splay or spread apart as a result of the spring force inherent in these branches in order thereby to engage onto a tissue part 25.

If the actuation lever 35 is now released, it passes into the position shown in FIG. 7 as a result of the action of the spring 48. In this position, the tissue part 25 is held by pressing the branches 46', 46" together by means of the front edge 65 of the guide tube 44 which is displaced forwardly by the action of the spring 48.

Reference Numerals 11 operator hand grip
12 instrument socket
12' back wall
13 instrument body
14 tube
15 central longitudinal axis (rotational axis)
16 cam
17 connection body
17' screw cap
17a shell half
17b shell half
18 fluid supply and removal line
19 electrical supply and control lines
20 actuation elements
21 wiper contact
22 slip rings
23 working channel
23' extension of the working channel in the connector body 17
23" front extension of the working channel in the cam 16
23'" rear extension of the working channel in the cam 16
23"" aperture in the rear end face of the instrument socket 12

24 working instrument
25 tissue part
26 RF cutting or coagulation instrument
26' cutting needle
27 connection lines
28 end surface
29 second working channel
30 extension
31 relief bores
32 spout
33 connector part
34 axial bore
35 actuation lever
36 latch collar
36' end surface
37 inclined plane
38 latching element
39 deployment spring
40 radial guide
41 release button
42 central longitudinal axis of the working channel 23
43 proximal connection end and actuation end
44 guide tube
45 working rod
46 working tool
46' clamping electrode
46" clamping electrode
47 base part
48 spring
49 bore
50 abutment collar
51 resetting spring
52 abutment collar engagement holder
52' projection
53 connection line
54 guide bar
55 guide
56 guide bore
57 keyboard or keypad
58 cavity
59 piston
60 double arrow
61 front surface
62 recess
63 bore for working rod 45 in the base part 47
64 abutment surface
65 front edge
66 clearance space
67 spigot part
68 spigot part
69 aperture
70 receiving bore
71 guide spigot
72 passage slot
73 passage slot
74 liquid flushing or suction channel
75 changeover valve
76 actuation element
77 connection line
78 connection line
79 drive
80 radial bore
81 control device
82 closure member
83 actuation member
84 beads
85 recess
86 connection lines

What is claimed is:

1. A multifunctional instrument for performing endoscopic operations having an instrument socket carrying an operator hand grip;
   wherein an instrument body is connected to the instrument socket via a rotational connection and comprises a multilumen tube that is guidable through a trocar into a body cavity of a patient;
   wherein the instrument body is rotatable about one of its longitudinal axes and is holdable in a selected rotational position;
   wherein at least one working channel and its central longitudinal axis are eccentrically arranged in a connection body of the instrument body relative to an axial rotational axis of the connection body;
   wherein a working channel axial extension or a working channel extension in the connection body is eccentrically arranged in a cam that is arranged within the instrument socket with radial clearance and is also arranged in an axially fixed manner with the cam being rotatable with the axis of the working channel axial extension about the rotational axis of the instrument body, but being substantially non-rotatably held about the axis of the working channel, in such a manner that the working channel axial extension in the cam can be brought into axial alignment with the working channel or the working channel extension in the connection body at any rotational position of the instrument body relative to the instrument socket;
   wherein the working channel axial extension provided in the cam is accessible in any rotational position of the cam through an aperture in a rear end face of the instrument socket;
   wherein the axis of the working channel or the working channel extension in the connection body and the axis of the working channel axial extension in the cam are held in axial alignment in any position of the instrument body by a suitable coupling of the connection body and of the cam; and
   wherein the rotational connection between the instrument socket and the instrument body is a stiff one and of a kind such that a rotational movement is possible but such that, in normal use, the selected rotational position is retained.

2. A multifunctional instrument in accordance with claim 1 wherein the instrument body is rotatable about its central longitudinal axis relative to the instrument socket fixedly connected to the operator hand grip.

3. A multifunctional instrument in accordance with claim 1 wherein an axial extension of the at least one working channel is eccentrically arranged in the connection body of the instrument body along with the at least one working channel.

4. A multifunctional instrument in accordance with claim 1 wherein the at least one working channel and its central longitudinal axis and an axial extension of the at least one working channel are eccentrically arranged in the connection body of the instrument body relative to an axial rotational axis of the tube as opposed to an axial rotational axis of the connection body.

5. A multifunctional instrument in accordance with claim 1, wherein a rod-shaped working instrument having a working tool provided at its distal end and a proximal connection end or actuation end that projects rearwardly from the instrument socket can be slid into the working channel from the rear and can be fixed in a working position.

6. A multifunctional instrument in accordance with claim 5, wherein the working instrument is rotatable, by more than 360°, within a working channel arrangement comprised of the working channel, the working channel axial extension, the working channel extension and the axial extension of the working channel extension.

7. A multifunctional instrument in accordance with claim 5, wherein the working instrument has a base part that is axially latchable with the instrument socket in the proximal end region of the working instrument, and wherein the base part carries a component at the front for actuating a working tool having at least two working positions, said component being axially displaceable.

8. A multifunctional instrument in accordance with claim 7, wherein an outwardly projecting actuation lever is arranged on the instrument socket in an axially displaceable manner and, when the working instrument is inserted, can be brought into axially fixed engagement with the component such that the component can be rearwardly displaced relative to the base part axially fixed at the instrument socket and the working tool can be actuated thereby.

9. A multifunctional instrument in accordance with claim 8, wherein an abutment collar engagement holder that is axially forwardly displaceable against a spring force is provided in the instrument socket and, as a result of the spring force, engages with the front surface of the actuation lever in an axial force transmitting manner.

10. A multifunctional instrument in accordance with claim 9, wherein, when the working instrument is slid in, the abutment collar engagement holder is loaded from behind in a force transmitting manner via a projection from the base part or via its latch collar, and directly after the abutment collar has come into engagement from behind with the actuation lever contacting the abutment collar engagement holder.

11. A multifunctional instrument in accordance with claim 7 wherein the component is axially displaceable rearwardly and against spring force.

12. A multifunctional instrument in accordance with claim 8 wherein an abutment collar engagement holder that is axially forwardly displaceable against a spring force is provided in the instrument socket and, as a result of the spring force, engages with the front surface of the actuation lever in a form-locked manner.

13. A multifunctional instrument in accordance with claim 5, wherein the working instrument, which has a base part, has a guide tube that is displaceable relative to the base part contains, in an axially relatively displaceable manner, a working rod with the working tool at its distal end, the working rod being either fixedly connected to the base part or forming one piece with the base part, the guide tube being displaceable in the forwardly displaced working position of the working instrument relative to the tube and relative to the working rod and between two axial positions, whereby the working tool is movable between an active and an inactive position, e.g. between a clamping position and a non-clamping position.

14. A multifunctional instrument in accordance with claim 13, wherein metallically conducting electrodes are provided at the front end of the working rod and are supplied with a radio frequency coagulation current, the electrodes being clamped against one another by the guide rod that is slid forward by the action of a spring and are unclamped by retracting the guide rod.

15. A multifunctional instrument in accordance with claim 13, wherein the actuation lever comprises a bore for axial passage of the guide tube and the guide tube comprises an abutment collar for the actuation lever that is positioned behind the actuation lever, wherein a distance adequate for the actuation movement of the guide tube is provided between the abutment collar and the base part.

16. A multifunctional instrument in accordance with claim 5, wherein a latching element is provided alongside an extension of the working channel in the instrument socket, is transversely displaceable against a spring force and, when the working instrument is slid into the instrument socket, enters into an axially secure latching engagement therewith.

17. A multifunctional instrument in accordance with claim 5, wherein fixing or latching means and actuation means for the instrument are provided in the cam, which is correspondingly hollow.

18. A multifunctional instrument in accordance with claim 17 wherein guide means for the fixing or latching means and guide means for the actuation means are provided in the correspondingly hollow cam.

19. A multifunctional instrument in accordance with claim 1,
  wherein the cam at the connection body is rotationally guided about an eccentric axis of the working channel and of the working channel axial extension in the cam that is axially aligned therewith, and is substantially held against rotation, by a radial actuation pin, inside the instrument socket;
  wherein, between the cam and walls of the instrument socket surrounding it, sufficient clearance space is present to allow the cam to also perform eccentric movement about the central longitudinal axis of the tube on rotation of the instrument body.

20. A multifunctional instrument in accordance with claim 1, wherein fixing or latching means and the actuation means for a working instrument are provided in the cam, which is correspondingly hollow.

21. A multifunctional instrument in accordance with claim 1, wherein the instrument body is formed to be releasable from the instrument socket.

22. A multifunctional instrument in accordance with claim 1, wherein the instrument body has two housing shell halves that are held together by one or more connection elements comprising at least one of the instrument socket, a clamping ring or a screw cap, and which are connected to the instrument socket in a rotatable manner, as well as an axially fixed manner.

23. A multifunctional instrument in accordance with claim 22, wherein the housing shell halves have spigot parts projecting towards the instrument socket that engage into a complementary, circular aperture at the front end of the instrument socket and are mounted there in a rotatable but axially fixed manner.

24. A multifunctional instrument in accordance with claim 22,
  wherein a connection part is arranged in the two housing shell halves at which at least one of the wiper contacts, the fluid supply or removal lines, the electrical supply and control lines, or an axial bore for the tube, as well as at least one of the working channel extension or the bore eccentric to the rotational axis for receiving a guide spigot of the cam centered relative to the axis of the working channel are provided;
  wherein at least one of passage slots for the fluid supply and removal lines or the electrical supply and control lines are provided in one of the housing shell halves.

25. A multifunctional instrument in accordance with claim 22 wherein the two housing shell halves are held together releasably.

26. A multifunctional instrument in accordance with claim 1, wherein a separate, small-lumen, liquid flushing or suction channel is provided in the tube and in the connection body and is connected in the connection body to fluid supply and removal lines.

27. A multifunctional instrument in accordance with claim 26, wherein a changeover valve is provided in the connection body and is controlled by an actuation element arranged at the working channel such that, when the working instrument is slid into the working channel extension in the connection body, it connects the small-lumen, liquid flushing or suction channel to the fluid supply and removal lines via a connection line and, when the working instrument is drawn out from the working channel extension, it connects the working channel to the fluid supply and removal lines via a connection line.

28. A multifunctional instrument in accordance with claim 1, wherein, when a working instrument is removed, the working channel is tightly sealable at a rear section and connectable to fluid supply and removal lines such that it is used as a liquid flushing or suction channel.

29. A multifunctional instrument for performing endoscopic operations having an instrument socket carrying an operator hand grip;

wherein an instrument body is connected to the instrument socket and comprises a multilumen tube that is guidable through a trocar into a body cavity of a patient;

wherein the instrument body is rotatable about one of its longitudinal axes and is holdable in the selected rotational position;

wherein at least one working channel and its central longitudinal axis are eccentrically arranged in a connection body of the instrument body relative to an axial rotational axis of the connection body;

wherein a working channel axial extension or a working channel extension in the connection body is eccentrically arranged in a cam that is arranged within the instrument socket with radial clearance and is also arranged in an axially fixed manner with the cam being rotatable with the axis of the working channel axial extension about the rotational axis of the instrument body, but being substantially non-rotatably held about the axis of the working channel, in such a manner that the working channel axial extension in the cam can be brought into axial alignment with the working channel or the working channel extension in the connection body at any rotational position of the instrument body relative to the instrument socket;

wherein the working channel axial extension provided in the cam is accessible in any rotational position of the cam through an aperture in a rear end face of the instrument socket;

wherein the axis of the working channel or the working channel extension in the connection body and the axis of the working channel axial extension in the cam are held in axial alignment in any position of the instrument body by a suitable coupling of the connection body and of the cam;

wherein the instrument body has a connection body that is rotatably mounted on the instrument socket and from which supply and removal lines and/or control lines branch off; and wherein the connection body, at its end remote from the instrument socket, is connected to the multilumen tube.

30. A multifunctional instrument in accordance with claim 29, wherein control lines run from the electrical actuation elements on the operator hand grip or from the instrument socket to the connection body via at least one of either wiper to slip ring contacts or flexible line sections.

31. A multifunctional instrument for performing endoscopic operations having an instrument socket carrying an operator hand grip;

wherein an instrument body is connected to the instrument socket and comprises a multilumen tube that is guidable through a trocar into a body cavity of a patient;

wherein the instrument body is rotatable about one of its longitudinal axes and is holdable in the selected rotational position;

wherein at least one working channel and its central longitudinal axis are eccentrically arranged in a connection body of the instrument body relative to an axial rotational axis of the connection body;

wherein a working channel axial extension or a working channel extension in the connection body is eccentrically arranged in a cam that is arranged within the instrument socket with radial clearance and is also arranged in an axially fixed manner with the cam being rotatable with the axis of the working channel axial extension about the rotational axis of the instrument body, but being substantially non-rotatably held about the axis of the working channel, in such a manner that the working channel axial extension in the cam can be brought into axial alignment with the working channel or the working channel extension in the connection body at any rotational position of the instrument body relative to the instrument socket;

wherein the working channel axial extension provided in the cam is accessible in any rotational position of the cam through an aperture in a rear end face of the instrument socket;

wherein the axis of the working channel or the working channel extension in the connection body and the axis of the working channel axial extension in the cam are held in axial alignment in any position of the instrument body by a suitable coupling of the connection body and of the cam;

wherein actuation elements for at least one of electrical control, or for switching a flushing or suction process on and off, or for mechanically actuating one or more working tools projecting from the distal end of the tube, are situated on the operator hand grip or on the instrument socket and can be actuated without the operator having to loosen his secure grip; and wherein at least one of:
line arrangements that are flexible in relation to the maximum amount of relative rotation that occurs;
at least one of electrical, hydraulic or pneumatic line arrangements; or
wiper to slip ring contacts;
are provided between the instrument socket and the instrument body rotatable relative thereto.

32. A multifunctional instrument for performing endoscopic operations having an instrument socket carrying an operator hand grip;

wherein an instrument body is connected to the instrument socket and comprises a multilumen tube that is guidable through a trocar into a body cavity of a patient;

wherein the instrument body is rotatable about one of its longitudinal axes and is holdable in the selected rotational position;

wherein at least one working channel and its central longitudinal axis are eccentrically arranged in a connection body of the instrument body relative to an axial rotational axis of the connection body;

wherein a working channel axial extension or a working channel extension in the connection body is eccentrically arranged in a cam that is arranged within the instrument socket with radial clearance and is also arranged in an axially fixed manner with the cam being rotatable with the axis of the working channel axial extension about the rotational axis of the instrument body, but being substantially non-rotatably held about the axis of the working channel, in such a manner that the working channel axial extension in the cam can be brought into axial alignment with the working channel or the working channel extension in the connection body at any rotational position of the instrument body relative to the instrument socket;

wherein the working channel axial extension provided in the cam is accessible in any rotational position of the cam through an aperture in a rear end face of the instrument socket;

wherein the axis of the working channel or the working channel extension in the connection body and the axis of the working channel axial extension in the cam are held in axial alignment in any position of the instrument body by a suitable coupling of the connection body and of the cam;

wherein actuation elements for at least one of electrical control, or for switching a flushing or suction process on and off, or for mechanically actuating one or more working tools projecting from the distal end of the tube, are situated on the operator hand grip or on the instrument socket and can be actuated without the operator having to loosen his secure grip; and, wherein the electrical actuation elements are provided in the form of a keypad at the rear side of the operator hand grip at the top and can be reached with the thumb of a hand that is holding the operator hand grip.

33. A multifunctional instrument in accordance with claim 32, wherein the working instrument possesses a retracted, rest position in which the working tool is retracted into the inside of the tube, as well as a working position in which the working tool projects beyond the distal end of the tube.

34. A multifunctional instrument in accordance with claim 33, wherein the working instrument latches in the forwardly displaced working position and is biased by spring force out of the working position in the direction of the retracted, rest position, and wherein the latching is releasable by means of a release device.

35. A multifunctional instrument in accordance with claim 34, wherein the spring force is produced by a resetting spring arrangement that is relaxed in the rest position and stressed in the working position.

* * * * *